United States Patent [19]

Carver

[11] Patent Number: 5,364,339
[45] Date of Patent: Nov. 15, 1994

[54] BED SORE PAD

[76] Inventor: Juanita Carver, 9866 Reagan Rd. #126, San Diego, Calif. 92126

[21] Appl. No.: 44,231

[22] Filed: Apr. 7, 1993

[51] Int. Cl.$^5$ .................. A61F 13/00; A61F 15/00
[52] U.S. Cl. .................. 602/47; 602/59; 128/888; 128/894; 5/461
[58] Field of Search .............. 602/41, 42, 47, 58, 602/59, 903; 128/887, 888, 893, 894; 5/461, 630, 652, 903; 604/336, 344, 332

[56] References Cited

U.S. PATENT DOCUMENTS

| | | | |
|---|---|---|---|
| 3,063,448 | 11/1962 | Scholl | 128/153 |
| 3,209,750 | 10/1965 | Levitt | 128/894 |
| 3,304,219 | 2/1967 | Nickerson | 161/162 |
| 3,392,081 | 7/1968 | Chavannes | 161/127 |
| 3,459,179 | 8/1969 | Olesen | 128/60 |
| 3,468,311 | 9/1969 | Gallagher | 128/296 |
| 3,556,096 | 1/1971 | Fuller | 128/171 |
| 3,606,886 | 9/1971 | Bittner | 128/894 |
| 3,608,961 | 9/1971 | Van Heck | 297/284 |
| 3,661,155 | 5/1972 | Lindan | 128/295 |
| 3,756,884 | 9/1973 | Hagino | 156/145 |
| 3,812,001 | 5/1974 | Ryan | 161/114 |
| 3,968,530 | 7/1976 | Dyson | 5/338 |
| 4,067,330 | 1/1978 | Roache | 128/149 |
| 4,425,676 | 1/1984 | Crane | 5/450 |
| 4,614,000 | 9/1986 | Mayer | 5/484 |
| 4,750,482 | 6/1988 | Sieverding | 128/156 |
| 4,959,059 | 9/1990 | Eilender et al. | 604/358 |
| 4,962,769 | 10/1990 | Garcia | 128/889 |

OTHER PUBLICATIONS

Air Cap Commercial Product Specification Sheet, Sealed Air Corporation (1988).
tesa Data Technical Data Sheet, tesa trick, Inc.
Arrlad 5–6450 product information sheet, Adhesives Research Inc. (Dec. 1992).

*Primary Examiner*—Randall L. Green
*Assistant Examiner*—Paul Prebilic
*Attorney, Agent, or Firm*—Charles E. Cates

[57] ABSTRACT

A stratiform pad for surrounding and protecting a bed sore from pressure while the patient is in bed. The pad comprises a median layer containing a closed cell air bubble film, a body-contacting layer bonded to one surface of the median layer to adhere the pad to the patient's body, and a bed-contacting layer bonded to the other surface of the median layer to adhere the pad to the bed surface. The pad contains an interior bed sore receiving aperture and provides sustained lift of the body away from the bed in the area of the sore, thus relieving the pain of pressure and providing space for the flow of healing air.

15 Claims, 1 Drawing Sheet

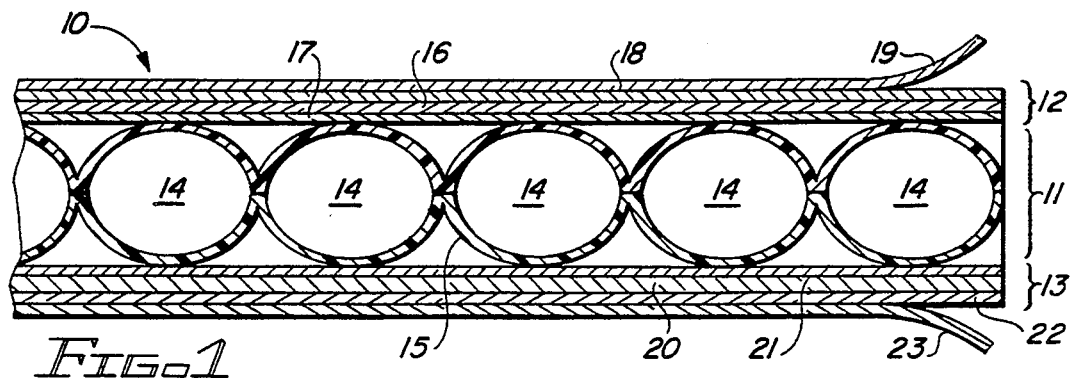
FIG. 1
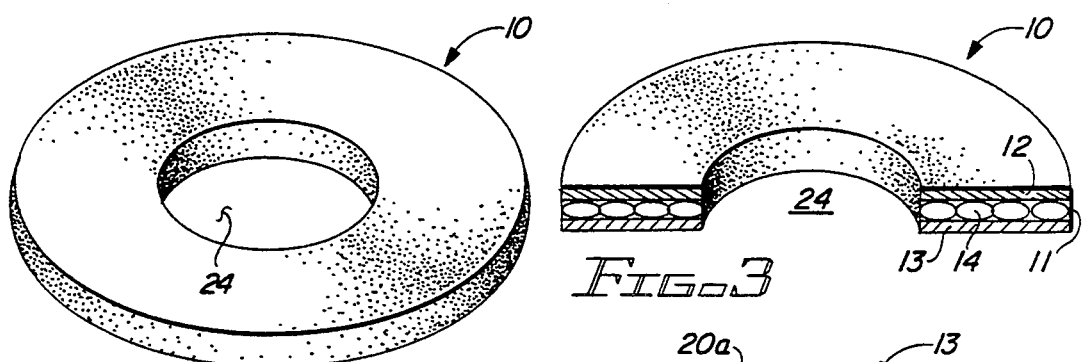
FIG. 2
FIG. 3
FIG. 6
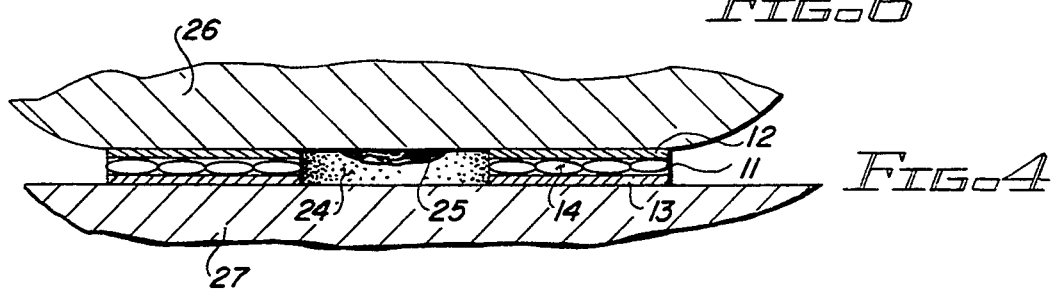
FIG. 4
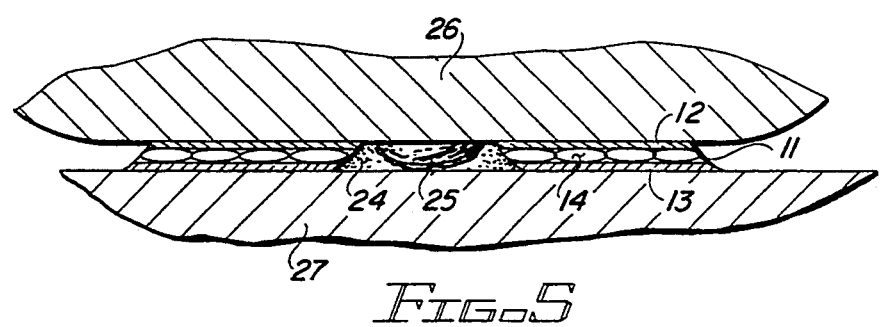
FIG. 5

BED SORE PAD

BACKGROUND OF THE INVENTION

The present invention relates generally to a pad for surrounding and protecting a bed sore on a person's body while in bed. The pad is effective in lifting the body away from the bed in the area of the sore, and thus promotes healing by avoiding pressure and providing a flow of air around the sore.

As Americans live longer, the number of hospitals and nursing homes for treating long-care patients increases constantly. One of the most common problems in the care of long-term bedridden patients is the possible development of decubitus ulcers or bed sores. They result from the pressure exerted on the skin and subcutaneous tissues by the skeletal bony prominences and the object on which the patient rests, such as a bed. The cutaneous tissues are progressively broken down leading to destruction of underlying soft tissue. Once this ulcer forms it is quite painful and very slow to heal. Bacterial infections are difficult to avoid and frequently prolong the healing process.

Numerous efforts have been put forth in the past to devise various cushions, pads, bandages, dressings, mattress modifications, and the like, for attempting to alleviate the pressure on bed sores and thereby promote healing. However, because of the materials used, or the configurations developed, or the expense of making and using the more elaborate devices, there has been no completely satisfactory solution to the problem. The prior devices have failed to offer a configuration which effectively avoids pressure against the sore and permits freedom of air flow around the sore.

It is the object of the present invention to provide an inexpensive disposable pad which is effective in absorbing and distributing the pressure of a patient's body and providing lift of the body away from the bed in the area of the bed sore.

It is another object of the invention to provide a pad which can be applied to the patient to avoid contact of the sore with the bed or bed coverings, while at the same time providing for a flow of air around the area of the sore.

It is a further object of the invention to provide a structure which maintains the cushioning material of the pad in its most effective configuration, despite the substantial pressure and distortion resulting from the weight of the patient's body against the bed in the area of the sore.

It is a still further object to provide a pad which relieves pressure, alleviates pain, promotes healing, and can be made of anti-static materials to protect sensitive hospital equipment.

Other objects and advantages will become apparent as the specification proceeds.

SUMMARY OF THE INVENTION

The present invention relates to a stratiform pad for surrounding and protecting a bed sore on a patient's body while in bed. The pad has component layers which are bonded together to form a unified pad containing at least the following layers: (1) A median layer comprising a closed cell air bubble film for absorbing and distributing the pressure of the patient's body and providing lift of the body away from the bed in the area of the bed sore; (2) a body-contacting layer bonded to a first surface of the median layer and adapted to adhere to the patient's body, said body-contacting layer being formed as an integral part of the pad to assist in preventing lateral movement of the median cushioning layer when pressed between the body and the bed; and (3) a bed-contacting layer bonded to the other surface of the median layer and adapted to cling or adhere to the bed or bed covering, said bed-contacting layer being formed as an integral part of the pad to assist in preventing lateral movement or shifting of the median cushioning layer. The pad is further characterized by having an interior aperture for receiving the bed sore and avoiding contact of the sore with the pad or the bed.

It is a feature of the invention that the pad has adhesive or gripping or clinging layers on both its surfaces, so that the pad is maintained in a fixed position both on the patient's body and on the surface of the bed. Hereafter the word adhere will be used to encompass this concept. With such an arrangement, the median cushioning layer resists lateral shifting or distortion from the pressure of the body, and as a result the full cushioning effect of the median layer is available for maintaining sustained lift of the patient's body away from the bed in the area of the sore.

The invention also includes the method of using said pad, comprising the steps of adhering a first surface of the closed air bubble film to the patient's body, with the interior aperture of the pad registering with the bed sore to avoid contact between the film and the sore, and adhering the other surface of the bubble film to the bed, whereby the film is held against lateral shifting and maintains sustained lift of the person's body away from the bed in the area of the sore.

BRIEF DESCRIPTION OF THE DRAWINGS

The objects, features and advantages of the invention will be apparent to those skilled in the art from the following detailed description, taken together with the accompanying drawings, in which:

FIG. 1 is a cross-sectional side view of the stratiform pad of the present invention, showing the component layers.

FIG. 2 is perspective view of a circular embodiment of the pad of the present invention, showing the interior aperture for receiving the bed sore.

FIG. 3 is a cross-sectional view, taken along line 3—3' of FIG. 2, showing the component layers of the stratiform pad of the invention.

FIG. 4 is a cross-sectional view of the pad in place on a patient's body.

FIG. 5 is a similar cross-sectional view, showing distortion which occurs (as in the prior art) if the pad is not adhered to the bed.

FIG. 6 is a cross-sectional view of an alternative embodiment.

DETAILED DESCRIPTION OF THE INVENTION

As shown in cross-section in FIG. 1, the present invention comprises a stratiform pad 10 containing a median layer 11, a body-contacting layer 12, and a bed-contacting layer 13. The median layer 11 is a closed cell air bubble film, in which series of airtight spaced apart air cells 14 are encapsulated in a strong plastic film 15, to provide the cushioning effect utilized in the invention.

Closed cell air bubble films are available in the industry for packaging purposes, and are made in a wide ranging scale of bubble sizes. For use in the present invention, the bubble size should be in the range of about 0.25" to 1.25" thick and from about 0.5" to 1.75" wide. Bubbles smaller than this would not provide the desired lift for most purposes, and larger bubbles would not be practical, considering the size of the pad, except in unusual applications, e.g., a very heavy patient for whom a larger and heavier size bubble may be specially made to accomodate the patient's weight. Preferably, the thickness should be from about 0.5" to 0.75", and the width from about 0.75" to 1.25". A very useful size for many application is a thickness of about 0.5" and a width of 1". It is important that the bubbles be of the closed cell variety, in order that the pad may maintain the lift necessary to keep the body separated from the bed at the point of the bed sore. Open cell pads made of foam rubber, thermoplastic foam, or other cushioning materials tend to conform to the shape of the supported part of the body, and therefore are not able to maintain the sustained lift of the body away from the bed.

In the preferred embodiment of the invention, the median layer 11 is a closed cell bubble pack in which the webbing film is made from a layer of nylon which has been coextruded between two layers of polyethylene. The nylon is extremely resistant to the passage of air, so that the bubbles retain their air (and their cushioning power) substantially longer and under greater pressure than other conventional films. The material is also fire retardant and antistatic, which is an important feature in a hospital environment. Further, it is not water absorbent, which is a factor when the patient is incontinent. Closed cell nylon barrier plastic film cushioning material of the type described is available from Sealed Air Corporation, of Fair Lawn, N.J., under the trademark AirCap.

The body-contacting layer 12 is composed of stabilizing tape 16 which is bonded to the upper surface of the median layer 11 by an adhesive layer 17. Tape 16 has an adhesive layer 18 on its upper surface for adhering the pad to the patient's body at the appropriate point. A peelable liner release layer 19 is applied to the adhesive layer 18 to protect the surface until ready for use.

The stabilizing tape 16 and its upper adhesive layer 18 is available as a unit in the form of standard adhesive tape made for adhering bandages and dressings to the body. Adhesive tapes suitable for use in the present invention are available from Johnson & Johnson, New Brunswick, N.J., under the trademarks Derma Care, for either cloth tapes or paper tapes. It is important that the tape be designed for application to the human skin, and therefore it should be porous, hypoallergenic and resistant to shredding or breaking.

The adhesive 17 for securing the adhesive tape 16,18 to the median cushioning layer 11 may be any of the known medical adhesives used for adhering dressings, prosthetic and other metal or plastic devices to the body or to each other. A medical adhesive suitable for the purposes of the present invention is sold by Dow Corning Corporation, Irvine, Calif., under the trademark Dow Corning 355 Medical Adhesive. It is supplied as a solution in a solvent and may be applied by brushing or spraying to the upper surface of the median layer 11 and the bottom surface of the adhesive tape 16,18, allowing for a short period of drying, and then pressing the two surfaces together.

In one embodiment of the invention, the adhesive tape 16,18 may be omitted and the top surface of the median layer 11 adhered directly to the skin by use of the medical adhesive 17, as described above. Use of the adhesive tape 16,18, however, provides a more conveniently marketable and stable product and also avoids problems for some patients who may be more sensitive to the medical adhesive solution than to adhesive tape.

In another embodiment, the medical adhesive 17 may be omitted, and the adhesive tape 16,18 bonded to the median layer 11 by heat sealing along the bounding edges of the two layers. Such heat sealing may be accomplished by use of a hot wire impulse sealing machine, such as sold by Jon-Ko Products, Inc, of San Diego, Calif., under the trademark TISH-200.

The bed-contacting layer 13 is preferably a non-slip siliconized cloth tape 20 having an adhesive coated on the side contacting the median layer 11. The opposite side is a pebbly surface that grips and clings to the bed surface. The layer 13 may also be coated on both sides with a pressure sensitive adhesive. An example of this preferred material is sold under the trademark TESA 4863 and described as embossed siliconized non-slip tape. The adhesive is thermosetting rubbers. The backing is siliconized cloth. It may be obtained from Tesa Tuck Inc., 324 South Union Drive, Sparta, Minn. 49345. In this embodiment the adhesive layer 21 on its upper side bonds the tape 20 to the lower surface of the median layer 11. The adhesive layer 22 on the bottom surface of tape 20 is for adhering the layer 13 to the surface of the bed. A peelable release liner 23 is applied to the bottom surface of adhesive layer 22 to protect the surface until ready for use.

In an alternative preferred embodiment shown in FIG. 6 the bed-contacting layer 13a is TESA 4863 (trademark of Tesa Tuck, Inc.) with the adhesive side offered to median layer 11 and the non-slip surface 20a presented to the bed surface. In FIG. 6 an embodiment showing the use of strips of TESA 4863 which may be made in any convenient form, FIG. 6 being only illustrative.

In the alternative preferred embodiment, the bed-contacting layer 13 is a tape which is coated on both sides with a pressure sensitive adhesive. A product suitable for use in the invention is made by Adhesives Research, Inc., of Glen Rock, Pa., under the trademark ARclad S-6450. It is a polyester film supported bonding tape coated on both sides with a rubber based pressure sensitive adhesive, and includes a siliconized Kraft release liner 23. The double coated tape may be applied to cover the entire bottom surface of the median layer 11, or it may be applied in strips at a sufficient number of points to ensure that the pad 10 adheres to the surface of the bed and is not allowed to slide laterally along the bed surface when the pressure of the weight of the patient's body is applied. The pressure sensitive adhesive should be strong enough to resist such lateral slippage, but at the same time it should be detachable to the extent of permitting the patient to lift his or her body (and attached pad) away from the bed when arising out of bed or changing positions.

In one embodiment of the invention, the double coated tape 13 may be omitted, and in its place a layer of medical adhesive may be coated, sprayed or brushed on the under surface of the median layer 11, to provide the adhesive for adhering the pad 10 to the bed. The coating thus applied to the bottom surface of the median layer would be covered by the release liner 23 to protect the surface until used.

The pad of the present invention may be provided in any convenient shape or configuration. As shown in FIGS. 2 and 3, a useful shape is circular, but it may also be rectangular, oval, or any other shape, depending on the part of the body being treated. It may also be adapted to wrap around a body part, such as an elbow or knee if the bed sore or pressure point to be protected is in that area.

As shown in FIGS. 2 and 3, the invention contemplates an interior aperture 24 in the pad 10 for surrounding and receiving the bed sore and avoiding contact of the sore with the pad. The aperture 24 should extend at least through layers 11 and 12 and can, if desired, extend also through layer 13, although this is not required.

In using the invention, the release liner 19 is peeled away from the upper surface of the body-contacting layer 12, and the pad is applied to the applicable body part in such manner that the adhesive layer 18 adheres the pad to the body. As shown in FIG. 4, the pad 10 is placed with the affliction or bed sore 25 centered within the aperture 24, so that the sore is surrounded, but not touched, by the pad. The release liner 23 is then peeled from the lower adhesive surface of bed-contacting layer 13, and the body 26 is lowered on to the bed 27. As shown in FIG. 4, the exposed adhesive surface of layer 13 contacts and adheres to the top surface of the bed 27, holding the pad against lateral shifting when the weight of the body 26 is applied. The lift supplied by the cushioning median layer 11 holds the bed sore 25 and the surrounding area of the body 26 away from and out of painful contact with the bed 27, and provides a path for flow of air around the sore to promote healing. Medications may also be applied through the aperture 24.

It is a feature of the invention that the pad 11 has adhesive layers 12 and 13 on its top and bottom surfaces, respectively, so that the pad is maintained in a fixed position both on the patient's body 26 and on the surface of the bed 27. With such arrangement, the median cushioning layer 11 resists lateral shifting or distortion from the pressure of the body, and as a result the full cushioning effect of the median layer 11 is available for maintaining sustained lift of the patient's body away from the bed in the area of the sore 25. Assuming that the principal pressure point of the body against the bed is located in the area of the bed sore 25, and assuming there were no adhesive surfaces 13 to resist slippage of the bottom of the pad 10 along the surface of the bed, the downward pressure of the body weight at the pressure point would cause lateral slippage of the bottom of the pad outwardly from the pressure point, as best shown in FIG. 5. This would cause loss of the vertical lift which the median cushioning layer is supposed to provide, again as shown in FIG. 5, and as a result there would be painful contact of the bed sore 25 with the bed 27 at the point 28, as well as a loss of air space for the healing flow of air.

The bed sore pad and method of the present invention provide the following features which are significantly advantageous in terms of effectiveness and economics:

1. The pad of the invention provides a sustained lift of the bed sore and the surrounding area of the body away from the bed, and thus provides for relief of the pain that is otherwise associated with the pressure on the sore.
2. Relief of pain promotes better sleeping for the patient, as well as a better appetite and an overall better health pattern.
3. The sustained lift permits the flow of air past the ulcerated skin, promoting healing.
4. The pad is made from inexpensive materials which are readily available on the market and can be assembled without the use of skilled labor or expensive machinery.
5. All the materials are fire retardant, antistatic and recyclable, which is important in a hospital environment.
6. The materials are also non-water absorbent, a feature which facilitates the treatment of patients who are incontinent.
7. The pad may be used not only for the protection and treatment of existing bed sores or afflictions, but it may also be used for the prevention of sores by application to pressure points where sores are known or expected to occur.

Although preferred embodiments of the invention have been described herein in detail, it will be understood by those skilled in the art that variations may be made thereto without departing from the spirit of the invention.

What is claimed is:

1. A stratiform pad for surrounding and protecting a bed sore on a person's body when in bed, said pad having component layers bonded together to form a unified pad, comprising:

a median layer comprising a closed cell air bubble film for absorbing and distributing the pressure of said person's body and providing lift of said body away from said bed in the area of said bed sore; a body-contacting layer bonded to a first surface of said median layer and adapted to adhere to said person's body, said body-contacting layer being formed as an integral part of said pad to assist in preventing lateral movement of said median layer when pressed between body and bed; and a bed-contacting layer bonded to a second surface of said median layer and adapted to adhere to said bed, said bed-contacting layer being formed as an integral part of said pad to assist in preventing lateral movement of said median layer, said pad being further characterized by having an interior aperture for receiving said bed sore and avoiding contact of the sore with the pad.

2. The pad of claim 1 wherein the said cells in said closed air bubble film have a thickness within the range of about 0.25" to about 1.5".

3. The pad of claim 1 wherein the said cells have a thickness of about 1".

4. The pad of claim 1 wherein the said closed cell air bubble film is constructed of a nylon-containing material.

5. The pad of claim 4 wherein the said nylon-containing material comprises layers of polyethylene and nylon.

6. The pad of claim 1 wherein said body-contacting layer is a hypoallergenic adhesive tape.

7. The pad of claim 6 wherein said hypoallergenic adhesive tape is bonded to said first surface of said median layer with a medical grade adhesive.

8. The pad of claim 1 wherein said body-contacting layer is a pressure sensitive adhesive coating on said first surface of said median layer.

9. The pad of claim 1 wherein said bed-contacting layer is a siliconized cloth tape coated on both sides with a pressure sensitive adhesive.

10. The pad of claim 1 wherein said bed-contacting layer is a pressure sensitive adhesive coating on said second surface of said median layer.

11. The pad of claim 1 wherein said component layers are bonded together with a heat sealed bond along their bounding edges.

12. The pad of claim 1 wherein said interior aperture comprises a central hole in said median and body-contacting layers.

13. A stratiform pad for surrounding and protecting a bed sore on a person's body when in bed, said pad having component layers bonded together to form a unified pad, comprising:
- a median layer comprising a closed cell air bubble nylon film, with a bubble size of about $\frac{1}{2}''$ to $\frac{3}{4}''$, for absorbing and distributing the pressure of said person's body and providing lift of said body away from said bed in the area of said bed sore;
- a body-contacting layer comprising a tape laid up on a first surface of said median layer, said tape having an adhesive coated upper surface facing away from said median layer and a bottom surface facing toward said median layer;
- a medical adhesive layer bonding said first surface of said median layer with said bottom surface of said body-contacting layer;
- a release liner secured to said adhesive coated surface of said body contacting layer for protecting said adhesive coated bottom surface prior to use;
- a bed-contacting layer comprising a tape coated on both sides with a pressure sensitive adhesive, said bed-contacting layer being bonded on one of its adhesive coated sides to a second surface of said median layer;
- a release liner secured to the other adhesive coated side of said bed-contacting layer for protecting said other adhesive coated side prior to use, said pad being further characterized by having an interior aperture for receiving said bed sore and avoiding contact of the sore with the pad.

14. The pad of claim 13 wherein the bubbles in said median layer have a thickness of approximately 1''.

15. The pad of claim 13 wherein the said median layer is constructed of layers of polyethylene and nylon.

* * * * *

UNITED STATES PATENT AND TRADEMARK OFFICE
CERTIFICATE OF CORRECTION

PATENT NO. : 5,364,339
DATED : November 15, 1994
INVENTOR(S) : Juanita Carver

It is certified that error appears in the above-identified patent and that said Letters Patent is hereby corrected as shown below:

Claim 2, column 6, line 44, "said cells" is deleted and --bubbles-- is inserted.

Claim 3, column 6, line 47, "said cells" is deleted and --bubbles-- is inserted.

Claim 13, column 8, line 4, --upper-- is inserted between "coated" and "surface".

Claim 13, column 8, line 6, "bottom" is deleted.

Signed and Sealed this

Eighth Day of August, 1995

Attest:

BRUCE LEHMAN

Attesting Officer    Commissioner of Patents and Trademarks